United States Patent
Kupar et al.

(10) Patent No.: US 9,115,275 B2
(45) Date of Patent: Aug. 25, 2015

(54) POLYOLEFIN COMPOSITION

(71) Applicant: Dow Global Technologies LLC, Midland, MI (US)

(72) Inventors: Mridula Kupar, Lake Jackson, TX (US); Mehmet Demirors, Pearland, TX (US); Pradeep Jain, Lake Jackson, TX (US); Philip P. Fontaine, Houston, TX (US); Douglas S. Ginger, Houston, TX (US); David T. Gillespie, Pearland, TX (US); Mustafa Bilgen, Manvel, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/141,835

(22) Filed: Dec. 27, 2013

(65) Prior Publication Data

US 2015/0148490 A1    May 28, 2015

Related U.S. Application Data

(60) Provisional application No. 61/746,151, filed on Dec. 27, 2012.

(51) Int. Cl.
*C08F 10/00*  (2006.01)
*C08L 23/06*  (2006.01)
*C08L 23/08*  (2006.01)

(52) U.S. Cl.
CPC .................................. *C08L 23/0815* (2013.01)

(58) Field of Classification Search
CPC ... B65D 51/26; C08F 210/16; C08F 4/64193; C08F 4/64186; C08J 5/18; C08L 23/0815
USPC .................................................. 525/191, 240
See application file for complete search history.

(56) References Cited

U.S. PATENT DOCUMENTS

| | | | | |
|---|---|---|---|---|
| 5,936,058 A | * | 8/1999 | Schauder ....................... | 528/272 |
| 8,101,685 B2 | * | 1/2012 | Jiang et al. ..................... | 525/191 |
| 8,106,127 B2 | * | 1/2012 | De Gracia et al. ............. | 525/191 |
| 2011/0282018 A1 | | 11/2011 | Klosin et al. | |

FOREIGN PATENT DOCUMENTS

WO    2007136496 A2    11/2007

OTHER PUBLICATIONS

Redlich, Chemical Engineering Science, 1972, pp. 1197-1203.
Balke, Chromatography of Polymers, 1992, Chapter 12, p. 180-198.
Balke, Chromatography Polym., 1992, Chapter 13, p. 199-219.
Zimm, J. Chem. Phys., 1948, vol. 16, p. 1099-1116.
Yau, Macromol. Symp., 2007, vol. 257, p. 29-45.
Monrabal, Macromol. Symp., 2007, vol. 257, p. 71-79.
Karjala, Annual Technical Conference—Society of Plastics Engineers, 2008, 66th, 887-891.

* cited by examiner

*Primary Examiner* — Nathan M Nutter

(57) ABSTRACT

The instant invention provides a polyolefin composition suitable for packaging applications, films, multilayer structures and packaging devices made therefrom. The polyolefin composition according to the present invention comprises: an ethylene/α-olefin interpolymer composition comprising (a) from 50 to 75 percent by weight of a first ethylene/α-olefin copolymer fraction having a density in the range of 0.894 to 0.908 g/cm³, a melt index ($I_2$) in the range of from 0.2 to 1 g/10 minutes, and (b) from 25 to 50 percent by weight of a second ethylene/α-olefin copolymer fraction, and wherein said ethylene/α-olefin interpolymer composition has a density in the range of 0.910 to 0.924 g/cm³, a melt index ($I_2$) in the range of from 0.5 to 2 g/10 minutes, a zero shear viscosity ratio (ZSVR) in the range of from 1.15 to 2.5, a molecular weight distribution, expressed as the ratio of the weight average molecular weight to number average molecular weight ($M_w/M_n$) in the range of from 2.0 to 4.0, and tan delta at 0.1 radian/second and 190° C. in the range of from 6 to 43.

10 Claims, 1 Drawing Sheet

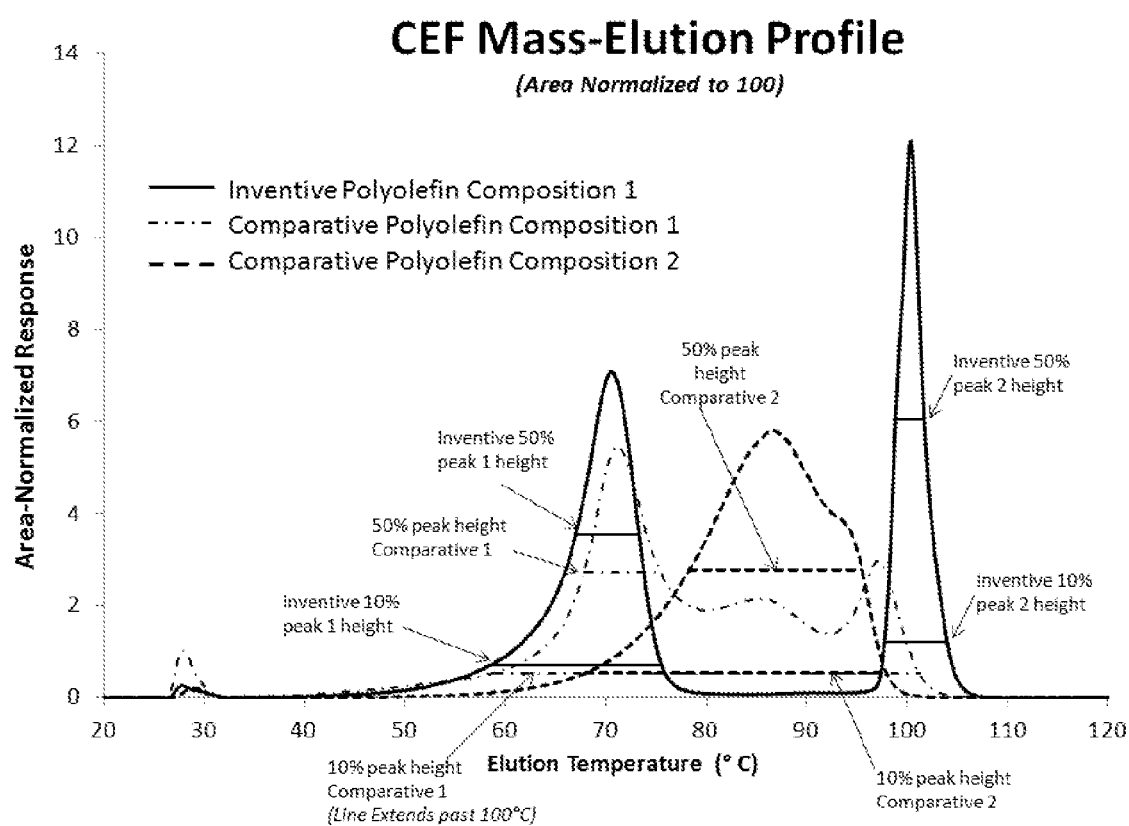

POLYOLEFIN COMPOSITION

REFERENCE TO RELATED APPLICATIONS

The present application claims the benefit of U.S. Provisional Application No. 61/746,151, filed on Dec. 27, 2012.

FIELD OF INVENTION

The instant invention relates to a polyolefin composition suitable for packaging applications, and method of producing the same.

BACKGROUND OF THE INVENTION

The use of polyolefin compositions in packaging applications is generally known. Any conventional method may be employed to produce such polyolefin compositions.

Various polymerization techniques using different catalyst systems have been employed to produce such polyolefin compositions suitable for packaging applications.

Despite the research efforts in developing compositions suitable for packaging applications, there is still a need for compositions suitable for packaging applications having a good balance of processability as well as improved mechanical properties. Additionally, there is a need for a method to produce such compositions suitable for packaging applications having a good balance of processability as well as improved mechanical properties.

SUMMARY OF THE INVENTION

The instant invention provides a polyolefin composition suitable for packaging applications, films, multilayer structures and packaging devices made therefrom.

In one embodiment, the instant invention provides a polyolefin composition suitable for packaging applications comprising: an ethylene/α-olefin interpolymer composition comprising (a) from 50 to 75 percent by weight of a first ethylene/α-olefin copolymer fraction having a density in the range of 0.894 to 0.908 g/cm$^3$, a melt index ($I_2$) in the range of from 0.2 to 1 g/10 minutes, and (b) from 25 to 50 percent by weight of a second ethylene/α-olefin copolymer fraction, and wherein said ethylene/α-olefin interpolymer composition has a density in the range of 0.910 to 0.924 g/cm$^3$, a melt index ($I_2$) in the range of from 0.5 to 2 g/10 minutes, a zero shear viscosity ratio (ZSVR) in the range of from 1.15 to 2.5, a molecular weight distribution, expressed as the ratio of the weight average molecular weight to number average molecular weight ($M_w/M_n$) in the range of from 2.0 to 4.0, and tan delta at 0.1 radian/second and 190° C. in the range of from 6 to 43, wherein said ethylene/α-olefin interpolymer composition has at least 2 peaks on elution profile via crystallization elution fractionation (CEF) procedure, wherein each peak comprises at least 25 weight percent of the total area of the elution profile, wherein the separation of the 2 peak positions are in the range of from 20 to 40° C., wherein a higher elution temperature peak is at an elution temperature greater than 90° C., and wherein a lower elution temperature peak is at an elution temperature in the range of from 50 to 80° C., and wherein the width of the higher elution temperature peak at 50 percent peak height is less than 4° C., and wherein the width of the higher elution temperature peak at 10 percent peak height is less than 9° C., and wherein the width of the lower elution temperature peak at 50 percent peak height is less than 8° C., and wherein the width of the lower elution temperature peak at 10 percent peak height is less than 25° C.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 1 illustrates the elution profile via crystallization elution fractionation (CEF) procedure for Inventive Example 1, Comparative Example 1 and Comparative Example 2.

DETAILED DESCRIPTION OF THE INVENTION

The instant invention provides a polyolefin composition suitable for packaging applications, films, multilayer structures and packaging devices made therefrom.

In one embodiment, the instant invention provides polyolefin composition suitable for packaging applications comprising: an ethylene/α-olefin interpolymer composition comprising (a) from 50 to 75 percent by weight of a first ethylene/α-olefin copolymer fraction having a density in the range of 0.894 to 0.908 g/cm$^3$, a melt index ($I_2$) in the range of from 0.2 to 1 g/10 minutes, and (b) from 25 to 50 percent by weight of a second ethylene/α-olefin copolymer fraction, and wherein said ethylene/α-olefin interpolymer composition has a density in the range of 0.910 to 0.924 g/cm$^3$, a melt index ($I_2$) in the range of from 0.5 to 2 g/10 minutes, a zero shear viscosity ratio (ZSVR) in the range of from 1.15 to 2.5, a molecular weight distribution, expressed as the ratio of the weight average molecular weight to number average molecular weight ($M_w/M_n$) in the range of from 2.0 to 4.0, and tan delta at 0.1 radian/second and 190° C. in the range of from 6 to 43, wherein said ethylene/α-olefin interpolymer composition has at least 2 peaks on elution profile via crystallization elution fractionation (CEF) procedure, wherein each peak comprises at least 25 weight percent of the total area of the elution profile, wherein the separation of the 2 peak positions are in the range of from 20 to 40° C., wherein a higher elution temperature peak is at an elution temperature greater than 90° C., and wherein a lower elution temperature peak is at an elution temperature in the range of from 50 to 80° C., and wherein the width of the higher elution temperature peak at 50 percent peak height is less than 4° C., and wherein the width of the higher elution temperature peak at 10 percent peak height is less than 9° C., and wherein the width of the lower elution temperature peak at 50 percent peak height is less than 8° C., and wherein the width of the lower elution temperature peak at 10 percent peak height is less than 25° C.

The polyolefin composition may further comprise additional components such as one or more other polymers. For example the polyolefin composition may further comprise one or more ethylene polymers, or one or more propylene based polymers, or combinations thereof.

In one embodiment, one or more ethylene/α-olefin interpolymer compositions and one or more propylene/α-olefin interpolymer compositions, as described herein, may be blended via any method known to a person of ordinary skill in the art including, but not limited to, dry blending, and melt blending via any suitable equipment, for example, an extruder, to produce the inventive packaging composition.

The polyolefin composition may further comprise additional components such as one or more additives. Such additives include, but are not limited to, antistatic agents, color enhancers, dyes, lubricants, fillers such as $TiO_2$ or $CaCO_3$, opacifiers, nucleators, processing aids, pigments, primary anti-oxidants, secondary anti-oxidants, UV stabilizers, antiblocks, slip agents, tackifiers, fire retardants, anti-microbial agents, odor reducer agents, anti-fungal agents, and combinations thereof. The polyolefin composition may contain from about 0.01 to about 10 percent by the combined weight of such additives, based on the weight of the ethylene-based polymer composition including such additives.

Ethylene/α-Olefin Interpolymer Composition

The ethylene/α-olefin interpolymer composition comprises (a) from 50 to 75 percent by weight of a first ethylene/α-olefin copolymer fraction having a density in the range of 0.894 to 0.908 g/cm$^3$, a melt index ($I_2$) in the range of from 0.2 to 1 g/10 minutes, and (b) from 25 to 50 percent by weight of a second ethylene/α-olefin copolymer fraction, and wherein said ethylene/α-olefin interpolymer composition has a density in the range of 0.910 to 0.924 g/cm$^3$, a melt index ($I_2$) in the range of from 0.5 to 2 g/10 minutes, a zero shear viscosity ratio (ZSVR) in the range of from 1.15 to 2.5, a molecular weight distribution, expressed as the ratio of the weight average molecular weight to number average molecular weight ($M_w/M_n$) in the range of from 2.0 to 4.0, and tan delta at 0.1 radian/second and 190° C. in the range of from 6 to 43, wherein said ethylene/α-olefin interpolymer composition has at least 2 peaks on elution profile via crystallization elution fractionation (CEF) procedure, wherein each peak comprises at least 25 weight percent of the total area of the elution profile, wherein the separation of the 2 peak positions are in the range of from 20 to 40° C., wherein a higher elution temperature peak is at an elution temperature greater than 90° C., and wherein a lower elution temperature peak is at an elution temperature in the range of from 50 to 80° C., and wherein the width of the higher elution temperature peak at 50 percent peak height is less than 4° C., and wherein the width of the higher elution temperature peak at 10 percent peak height is less than 9° C., and wherein the width of the lower elution temperature peak at 50 percent peak height is less than 8° C., and wherein the width of the lower elution temperature peak at 10 percent peak height is less than 25° C.

The ethylene/α-olefin interpolymer composition comprises (a) less than or equal to 100 percent, for example, at least 70 percent, or at least 80 percent, or at least 90 percent, of the units derived from ethylene; and (b) less than 30 percent, for example, less than 25 percent, or less than 20 percent, or less than 10 percent, by weight of units derived from one or more α-olefin comonomers. The term "ethylene/α-olefin interpolymer composition" refers to a polymer that contains more than 50 mole percent polymerized ethylene monomer (based on the total amount of polymerizable monomers) and, optionally, may contain at least one comonomer.

The α-olefin comonomers typically have no more than 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-hexene and 1-octene.

The ethylene/α-olefin interpolymer composition is characterized by having a Comonomer Distribution Constant in the range of from 50 to 500, for example from 100 to 450, or from 150 to 450, or from 190 to 450, or from 100 to 400.

The ethylene-based polymer composition is characterized by having a zero shear viscosity ratio (ZSVR) in the range of from 1.15 to 2.5, for example, from 1.15 to, 2.0, from 1.2 to 2.0, or in the alternative from 1.2 to 1.8.

The ethylene/α-olefin interpolymer composition is characterized by having a tan delta at 0.1 radian/second, determined at 190° C., in the range of from 6 to 43, for example from 6 to 40, from 6 to 35, from 6 to 30, from 10 to 40, from 10 to 35, or from 10 to 30.

The ethylene/α-olefin interpolymer composition has a density in the range of 0.910 to 0.924 g/cm$^3$, for example from 0.912 to 0.920 g/cm$^3$. For example, the density can be from a lower limit of 0.910, 0.912, or 0.914 g/cm$^3$ to an upper limit of 0.924, 0.922, or 0.920 g/cm$^3$.

The first ethylene/α-olefin copolymer fraction has a density in the range of 0.894 to 0.908 g/cm$^3$, for example from 0.896 to 0.906 g/cm$^3$. For example, the density can be from a lower limit of 0.894, 0.896, 0.898, 0.900 g/cm$^3$ to an upper limit of 0.908, 0.906, 0.904, or 0.902 g/cm$^3$.

The second ethylene/α-olefin copolymer fraction has a density in the range of 0.940 to 0.955 g/cm$^3$, for example from 0.943 to 0.953 g/cm$^3$. For example, the density can be from a lower limit of 0.940, 0.943, or 0.945 g/cm$^3$ to an upper limit of 0.955, 0.953, 0.952, or 0.951 g/cm$^3$. The density of the second ethylene/α-olefin copolymer fraction can be approximated based on the density of a polymer prepared in a single reactor under the same polymerisation conditions of the second ethylene/α-olefin copolymer fraction in the absence of the first ethylene/α-olefin copolymer fraction.

The ethylene/α-olefin interpolymer composition has a molecular weight distribution, expressed as the ratio of the weight average molecular weight to number average molecular weight ($M_w/M_n$) in the range of from 2.0 to 4.0. For example, the molecular weight distribution ($M_w/M_n$) can be from a lower limit of 2.0, 2.1, or 2.2 to an upper limit of 2.6, 2.8, 3.0, 3.5, or 4.0.

The first ethylene/α-olefin copolymer fraction has a molecular weight distribution ($M_w/M_n$) in the range of from 1.5 to 3.5, for example from 2 to 3. For example, the molecular weight distribution ($M_w/M_n$) can be from a lower limit of 1.5, 1.7, 2.0, 2.1, or 2.2 to an upper limit of 2.5, 2.6, 2.8, 3.0, or 3.5.

The second ethylene/α-olefin copolymer fraction has a molecular weight distribution ($M_w/M_n$) in the range of from 1.5 to 3.0, for example from 2 to 3. For example, the molecular weight distribution ($M_w/M_n$) can be from a lower limit of 1.5, 1.7, 2.0, 2.1, or 2.2 to an upper limit of 2.5, 2.6, 2.8, or 3.0.

The ethylene/α-olefin interpolymer composition has a melt index ($I_2$) (at 190° C./2.16 kg) in the range of from 0.5 to 2.5 g/10 minutes, for example from 0.5 to 2.0 g/10 minutes, or from 0.5 to 1.5 g/10 minutes, or from 0.5 to 1.0 g/10 minutes. For example, the melt index ($I_2$ at 190° C./2.16 kg) can be from a lower limit of 0.5, 0.6, or 0.7 g/10 minutes to an upper limit of 0.9, 1.0, 1.2, 1.5, 1.6, 1.7, 1.8, 1.9, 2.0, 2.5 g/10 minutes.

The first ethylene/α-olefin copolymer fraction has a melt index ($I_2$) (at 190° C./2.16 kg) in the range of from 0.1 to 0.8 g/10 minutes, for example from 0.2 to 0.6 g/10 minutes, or from 0.3 to 0.5 g/10 minutes, or from 0.3 to 0.4 g/10 minutes.

The ethylene/α-olefin interpolymer composition has vinyl unsaturation of less than 0.15, for example less than 0.1, or less than 0.05 vinyls per one thousand carbon atoms present in the backbone of the ethylene-based polymer composition.

The ethylene/α-olefin interpolymer composition has normalized intrinsic Elmendorf tear greater than 375 g/mil, for example greater than 400 g/mil or 425 g/mil.

The ethylene/α-olefin interpolymer composition may further comprise additional components such as one or more additives. Such additives include, but are not limited to, antistatic agents, color enhancers, dyes, lubricants, fillers such as $TiO_2$ or $CaCO_3$, opacifiers, nucleators, processing aids, pigments, primary anti-oxidants, secondary anti-oxidants, UV stabilizers, anti-blocks, slip agents, tackifiers, fire retardants, anti-microbial agents, odor reducer agents, anti-fungal agents, and combinations thereof. The ethylene/α-olefin interpolymer composition may contain from about 0.1 to about 10 percent by the combined weight of such additives, based on the weight of the ethylene-based polymer composition including such additives.

In one embodiment, ethylene/α-olefin interpolymer composition has at least 2 peaks on elution profile via crystallization elution fractionation (CEF) procedure, wherein each peak comprises at least 25 weight percent of the total area of the elution profile, and wherein the separation of the 2 peak positions are in the range of from 20 to 40° C., and wherein a higher elution temperature peak is at an elution temperature greater than 90° C., and wherein a lower elution temperature peak is at an elution temperature in the range of from 50 to 80° C., and wherein the width of the higher elution temperature peak at 50 percent peak height is less than 4° C., and wherein the width of the higher elution temperature peak at 10 percent peak height is less than 9° C., and wherein the width of the lower elution temperature peak at 50 percent peak height is less than 8° C., and wherein the width of the lower elution temperature peak at 10 percent peak height is less than 25° C.

Any conventional polymerization processes may be employed to produce the ethylene/α-olefin interpolymer composition. Such conventional polymerization processes include, but are not limited to, solution polymerization process, using one or more conventional reactors e.g. loop reactors, isothermal reactors, stirred tank reactors, batch reactors in parallel, series, and/or any combinations thereof.

The ethylene/α-olefin interpolymer composition may, for example, be produced via solution phase polymerization process using one or more loop reactors, isothermal reactors, and combinations thereof.

In general, the solution phase polymerization process occurs in one or more well-mixed reactors such as one or more isothermal loop reactors or one or more adiabatic reactors at a temperature in the range of from 115 to 250° C.; for example, from 115 to 200° C., and at pressures in the range of from 300 to 1000 psi; for example, from 400 to 750 psi. In one embodiment in a dual reactor, the temperature in the first reactor is in the range of from 115 to 190° C., for example, from 115 to 150° C., and the second reactor temperature is in the range of 150 to 200° C., for example, from 170 to 195° C. In another embodiment in a single reactor, the temperature in the reactor is in the range of from 115 to 190° C., for example, from 115 to 150° C. The residence time in solution phase polymerization process is typically in the range of from 2 to 30 minutes; for example, from 10 to 20 minutes. Ethylene, solvent, hydrogen, one or more catalyst systems, optionally one or more cocatalysts, and optionally one or more comonomers are fed continuously to one or more reactors. Exemplary solvents include, but are not limited to, isoparaffins. For example, such solvents are commercially available under the name ISOPAR E from ExxonMobil Chemical Co., Houston, Tex. The resultant mixture of the ethylene/alpha-olefin interpolymer and solvent is then removed from the reactor and the ethylene/alpha-olefin interpolymer is isolated. Solvent is typically recovered via a solvent recovery unit, i.e. heat exchangers and vapor liquid separator drum, and is then recycled back into the polymerization system.

In one embodiment, the ethylene/α-olefin interpolymer composition may be produced via solution polymerization in a dual reactor system, for example a dual loop reactor system, wherein ethylene and optionally one or more α-olefins are polymerized in the presence of one or more catalyst systems. Additionally, one or more cocatalysts may be present.

In another embodiment, the ethylene/alpha-olefin interpolymers may be produced via solution polymerization in a single reactor system, for example a single loop reactor system, wherein ethylene and optionally one or more α-olefins are polymerized in the presence of one or more catalyst systems.

An exemplary catalyst system suitable for producing the first ethylene/a olefin interpolymer can be a catalyst system comprising a procatalyst component comprising a metal-ligand complex of formula (IA):

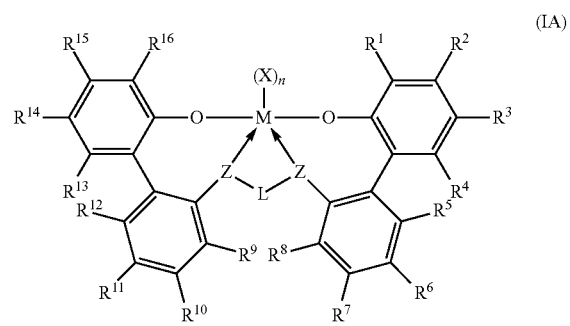

(IA)

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (IA) is, overall, neutral; and Each Z independently is O, S, $N(C_1-C_{40})$hydrocarbyl, or $P(C_1-C_{40})$hydrocarbyl; and The Z-L-Z fragment is comprised of formula (II):

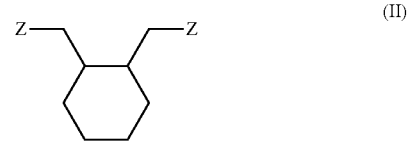

(II)

$R^{1-16}$ are selected from the group consisting of a $(C_1-C_{40})$ hydrocarbyl, $(C_1-C_{40})$heterohydrocarbyl, $Si(R^C)_3$, $Ge(R^C)_3$, $P(R^P)_2$, $N(R^N)_2$, $OR^C$, $SR^C$, $NO_2$, $CN$, $CF_3$, $R^CS(O)$—, $R^CS(O)_2$—, $(R^C)_2C=N$—, $R^CC(O)O$—, $R^COC(O)$—, $R^CC(O)N(R)$—, $(R^C)_2NC(O)$—, halogen atom, hydrogen atom, and combination thereof.

Optionally two or more R groups (from $R^{9-13}$ or $R^{4-8}$) can combine together into ring structures, with such ring structures having from 3 to 50 atoms in the ring excluding any hydrogen atoms.

Each of the aryl, heteroaryl, hydrocarbyl, heterohydrocarbyl, $Si(R^C)_3$, $Ge(R^C)_3$, $P(R^P)_2$, $N(R^N)_2$, $OR^C$, $SR^C$, $R^CS(O)$—, $R^CS(O)_2$—, $(R^C)_2C=N$—, $R^CC(O)O$—, $R^COC(O)$—, $R^CC(O)N(R)$—, $(R^C)_2NC(O)$—, hydrocarbylene, and heterohydrocarbylene groups independently is unsubstituted or substituted with one or more $R^S$ substituents; and Each $R^S$ independently is a halogen atom, polyfluoro substitution, perfluoro substitution, unsubstituted $(C_1$-$C_{18})$alkyl, $F_3C$—, $FCH_2O$—, $F_2HCO$—, $F_3CO$—, $R_3Si$—, $R_3Ge$—, $RO$—, $RS$—, $RS(O)$—, $RS(O)_2$—, $R_2P$—, $R_2N$—, $R_2C$=N—, NC—, RC(O)O—, ROC(O)—, RC(O)N(R)—, or $R_2NC(O)$—, or two of the $R^S$ are taken together to form an unsubstituted $(C_1$-$C_{18})$alkylene, wherein each R independently is an unsubstituted $(C_1$-$C_{18})$alkyl.

In one embodiment the catalyst system suitable for producing the first ethylene/α olefin interpolymer can be a catalyst system comprising bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

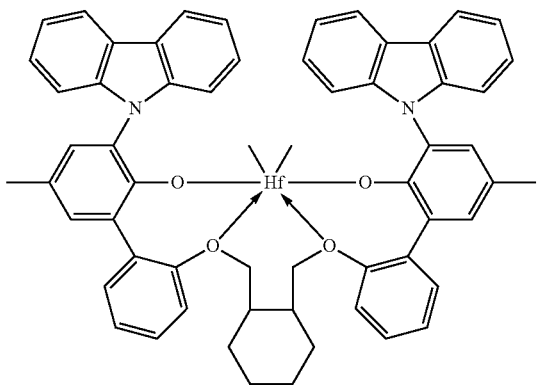

An exemplary catalyst system suitable for producing the second ethylene/α olefin interpolymer can be a catalyst system comprising a procatalyst component comprising a metal-ligand complex of formula (TB):

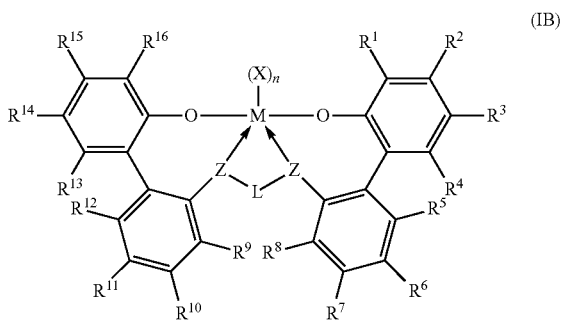

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (TB) is, overall, neutral; and Each Z independently is O, S, N$(C_1$-$C_{40})$hydrocarbyl, or P$(C_1$-$C_{40})$hydrocarbyl; and L is $(C_3$-$C_{40})$hydrocarbylene or $(C_3$-$C_{40})$heterohydrocarbylene, wherein the $(C_3$-$C_{40})$hydrocarbylene has a portion that comprises a 3-carbon atom to 10-carbon atom linker backbone linking the Z atoms in formula (IB) (to which L is bonded) and the $(C_3$-$C_{40})$heterohydrocarbylene has a portion that comprises a 3-atom to 10-atom linker backbone linking the Z atoms in formula (IB), wherein each of the from 3 to 10 atoms of the 3-atom to 10-atom linker backbone of the $(C_3$-$C_{40})$heterohydrocarbylene independently is a carbon atom or heteroatom, wherein each heteroatom independently is O, S, S(O), S(O)$_2$, Si$(R^C)_2$, Ge$(R^C)_2$, P$(R^P)$, or N$(R^N)$, wherein independently each $R^C$ is $(C_1$-$C_{30})$hydrocarbyl, each $R^P$ is $(C_1$-$C_{30})$hydrocarbyl; and each $R^N$ is $(C_1$-$C_{30})$hydrocarbyl or absent; and $R^1$, $R^{16}$, or both comprise of formula (III), and preferably $R^1$ and $R^{16}$ are the same; and

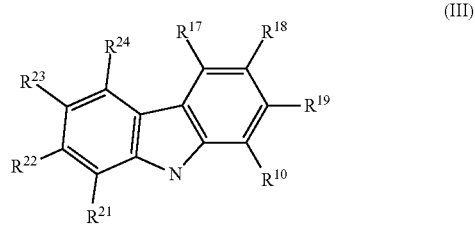

(III)

$R^{1-24}$ are selected from the group consisting of a $(C_1$-$C_{40})$hydrocarbyl, $(C_1$-$C_{40})$heterohydrocarbyl, Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$—, halogen atom, hydrogen atom, and combination thereof.

When $R^{22}$ is H, then $R^{19}$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and When $R^{19}$ is H, then $R^{22}$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and Preferably, $R^{22}$ and $R^{19}$ are both a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and When $R^8$ is H, then $R^9$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and When $R^9$ is H, then $R^8$ is a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and Preferably, $R_8$ and $R_9$ are both a $(C_1$-$C_{40})$hydrocarbyl; $(C_1$-$C_{40})$heterohydrocarbyl; Si$(R^C)_3$, Ge$(R^C)_3$, P$(R^P)_2$, N$(R^N)_2$, $OR^C$, $SR^C$, $NO_2$, CN, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$— or halogen atom; and Optionally two or more R groups (from $R^{9-13}$ or $R^{4-8}$) can combine together into ring structures, with such ring structures having from 3 to 50 atoms in the ring excluding any hydrogen atoms.

Each of the aryl, heteroaryl, hydrocarbyl, heterohydrocarbyl, Si$(R^C)_3$, Ge$(R^C)_3$, P$(R^P)_2$, N$(R^N)_2$, O$R^C$, S$R^C$, $R^C$S(O)—, $R^C$S(O)$_2$—, $(R^C)_2$C=N—, $R^C$C(O)O—, $R^C$OC(O)—, $R^C$C(O)N(R)—, $(R^C)_2$NC(O)—, hydrocarbylene, and heterohydrocarbylene groups independently is unsubstituted or substituted with one or more $R^S$ substituents; and Each $R^S$ independently is a halogen atom, polyfluoro substitution, perfluoro substitution, unsubstituted $(C_1-C_{18})$alkyl, $F_3C$—, $FCH_2O$—, $F_2HCO$—, $F_3CO$—, $R_3Si$—, $R_3Ge$—, RO—, RS—, RS(O)—, RS(O)$_2$—, $R_2P$—, $R_2N$—, $R_2C$=N—, NC—, RC(O)O—, ROC(O)—, RC(O)N(R)—, or $R_2NC(O)$—, or two of the $R^S$ are taken together to form an unsubstituted $(C_1-C_{18})$alkylene, wherein each R independently is an unsubstituted $(C_1-C_{18})$alkyl.

Optionally two or more R groups (from $R^{20-24}$) can combine together into ring structures, with such ring structures having from 3 to 50 atoms in the ring excluding any hydrogen atoms.

In one embodiment the catalyst system suitable for producing the second ethylene/a olefin interpolymer can be a catalyst system comprising ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

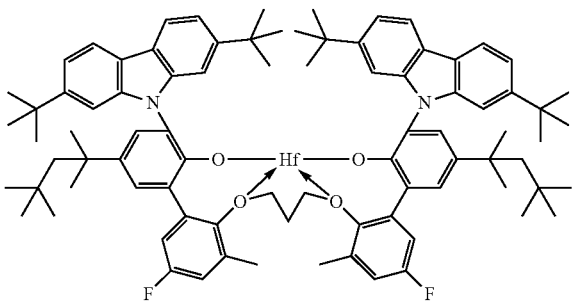

Co-Catalyst Component

The above described catalyst systems can be rendered catalytically active by contacting it to, or combining it with, the activating co-catalyst or by using an activating technique such as those that are known in the art for use with metal-based olefin polymerization reactions. Suitable activating co-catalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 metal compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri$((C_1-C_{10})$alkyl)aluminum or tri$((C_6-C_{18})$aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris$((C_1-C_{20})$hydrocarbyl)borate (e.g., trityl tetrafluoroborate) or a tri$((C_1-C_{20})$hydrocarbyl)ammonium tetra$((C_1-C_{20})$hydrocarbyl)borane (e.g., bis(octadecyl)methylammonium tetrakis(pentafluorophenyl)borane). As used herein, the term "ammonium" means a nitrogen cation that is a $((C_1-C_{20})$hydrocarbyl)$_4$N+, a $((C_1-C_{20})$hydrocarbyl)$_3$N(H)$^+$, a $((C_1-C_{20})$hydrocarbyl)$_2$N(H)$_2^+$, $(C_1-C_{20})$hydrocarbylN(H)$_3^+$, or N(H)$_4^+$, wherein each $(C_1-C_{20})$hydrocarbyl may be the same or different.

Exemplary combinations of neutral Lewis acid activating co-catalysts include mixtures comprising a combination of a tri$((C_1-C_4)$alkyl)aluminum and a halogenated tri$((C_6-C_{18})$aryl)boron compound, especially a tris(pentafluorophenyl)borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex):(tris(pentafluoro-phenylborane): (alumoxane) [e.g., (Group 4 metal-ligand complex):(tris(pentafluoro-phenylborane): (alumoxane)] are from 1:1:1 to 1:10:30, other exemplary embodiments are from 1:1:1.5 to 1:5:10.

Many activating co-catalysts and activating techniques have been previously taught with respect to different metal-ligand complexes in the following USPNs: U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163,907. Examples of suitable hydrocarbyloxides are disclosed in U.S. Pat. No. 5,296,433. Examples of suitable Bronsted acid salts for addition polymerization catalysts are disclosed in U.S. Pat. No. 5,064,802; U.S. Pat. No. 5,919,983; U.S. Pat. No. 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, the above described catalyst systems can be activated to form an active catalyst composition by combination with one or more cocatalyst such as a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to modified methyl aluminoxane (MMAO), bis(hydrogenated tallow alkyl)methyl, tetrakis(pentafluorophenyl)borate(1-) amine (RIBS-2), triethyl aluminum (TEA), and any combinations thereof.

In some embodiments, one or more of the foregoing activating co-catalysts are used in combination with each other. An especially preferred combination is a mixture of a tri(($C_1$-$C_4$)hydrocarbyl)aluminum, tri(($C_1$-$C_4$)hydrocarbyl)borane, or an ammonium borate with an oligomeric or polymeric alumoxane compound.

End-Use Applications of the Polyolefin Composition

The polyolefin compositions according to the present invention may be used in any food, consumer and industrial packaging applications such as construction film, heavy duty shipping sacks, protective film, waste management, and agricultural films, which require film with high dart, puncture and/or tear resistance properties.

The polyolefin compositions according to the present invention may be formed into a film, a sheet, or a multilayer structure. Such multilayer structures typically comprise one or more film layers or sheets comprising the inventive polyolefin compositions. The multilayer structure may further comprise one or more layers comprising one or more polyamides, one or more polyesters, one or more polyolefins, and combinations thereof.

Inventive polyolefin compositions according to the present invention are characterized by two or more of the followings: (a) having a Dart impact A of at least 1000 g, measured according to ASTM D1709, when said polyolefin composition is formed into a monolayer blown film having a thickness of 1 mil; (b) having a Dart impact B of at least 400 g, measured according to ASTM D1709, when said polyolefin composition is formed into a monolayer blown film having a thickness of 1 mil; and/or (c) having a normalized machine direction Elmendorf tear of at least 250 g/mil, measured according to ASTM D1922, when said polyolefin composition is formed into a monolayer blown film having a thickness of 1 mil.

The polyolefin composition according to present invention can further comprise 5 to 20 percent by weight of low density polyethylene (LDPE), and wherein the Dart Impact A is greater than 275 g, preferably greater than 300 g measured according to ASTM D1709, when said polyolefin composition is formed into a monolayer blown film having a thickness of 1 mil.

EXAMPLES

The following examples illustrate the present invention but are not intended to limit the scope of the invention.

Inventive Polyolefin Composition 1

Inventive polyolefin composition 1 (IPC-1) comprises an ethylene-octene interpolymer, having a density of approximately 0.919 g/cm$^3$, a melt index ($I_2$), measured at 190° C. and 2.16 kg, of approximately 0.96 g/10 minutes, an melt flow ratio ($I_{10}/I_2$) of approximately 6.3. Additional properties of IPC-1 were measured, and are reported in Table 2.

IPC-1 was prepared via solution polymerization in a dual loop reactor system in the presence of a first catalyst system, as described below, in the first and a second catalyst system, as described below, in the second reactor.

The first catalyst system comprises bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

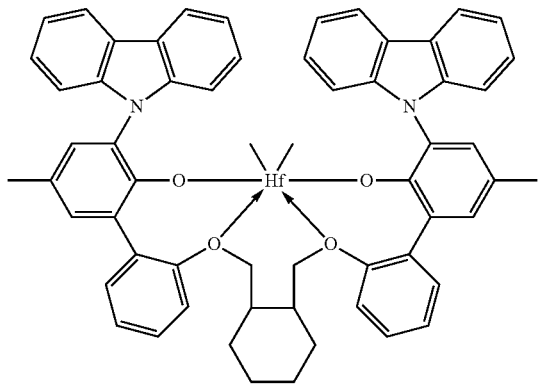

The second catalyst system comprises ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

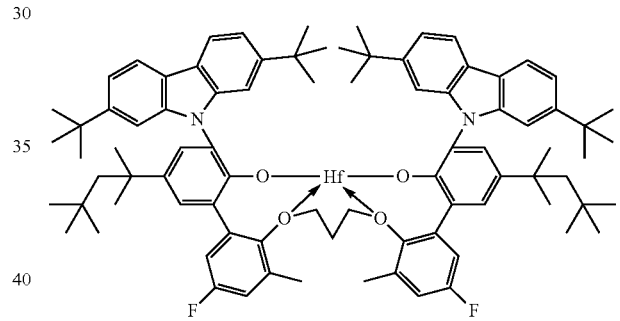

The polymerization conditions for IPC-1 are reported in Table 1. Referring to Table 1, MMAO is modified methyl aluminoxane; and RIBS-2 is bis(hydrogenated tallow alkyl)methyl, tetrakis(pentafluorophenyl)borate(1-)amine, used as cocatalysts.

Inventive Polyolefin Composition 2

Inventive polyolefin composition 2 (IPC-2) comprises an ethylene-octene interpolymer, having a density of approximately 0.918 g/cm$^3$, a melt index ($I_2$), measured at 190° C. and 2.16 kg, of approximately 0.74 g/10 minutes, an melt flow ratio ($I_{10}/I_2$) of approximately 6.1. Additional properties of IPC-2 were measured, and are reported in Table 2.

IPC-2 was prepared via solution polymerization in a dual loop reactor system in the presence of a first catalyst system, as described below, in the first and a second catalyst system, as described below, in the second reactor.

The first catalyst system comprises bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

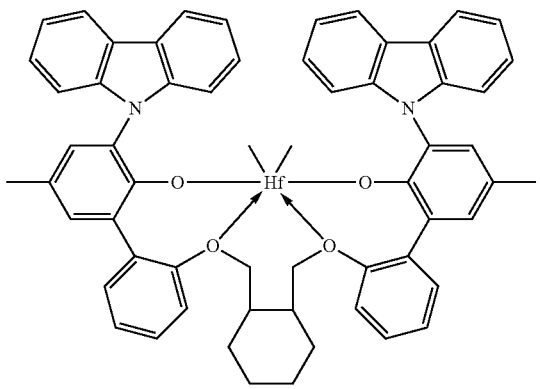

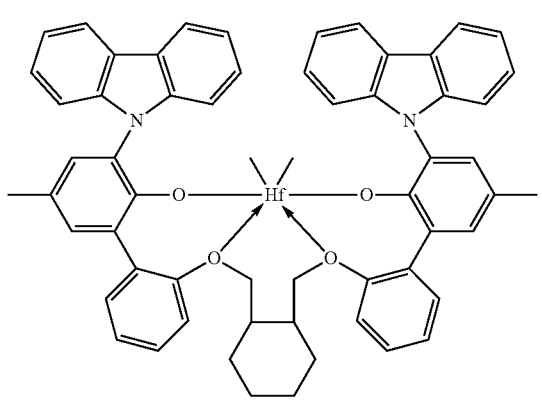

The second catalyst system comprises ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

The second catalyst system comprises ((3-(2,7-di-tert-butyl-9H-carbazol-9-yl)-2'-(3-((3'-(2,7-di-tert-butyl-9H-carbazol-9-yl)-5-fluoro-2'-hydroxy-3-methyl-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-yl)oxy)hafnium (IV) dimethyl, represented by the following formula:

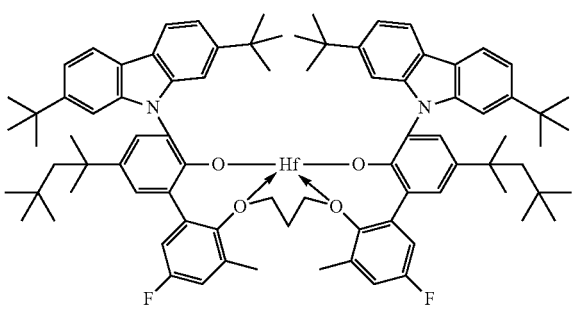

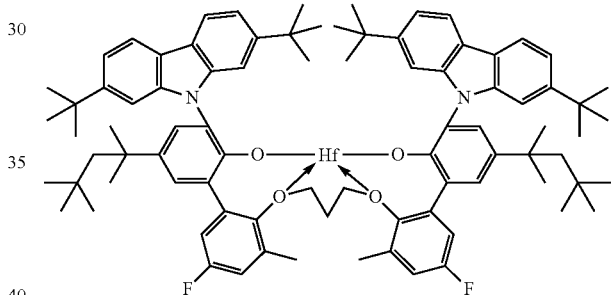

The polymerization conditions for IPC-2 are reported in Table 1. Referring to Table 1, MMAO is modified methyl aluminoxane; and RIBS-2 is bis(hydrogenated tallow alkyl) methyl, tetrakis(pentafluorophenyl)borate(1-)amine, used as cocatalysts.

Inventive Polyolefin Composition 3

Inventive polyolefin composition 3 (IPC-3) comprises an ethylene-octene interpolymer, having a density of approximately 0.918 g/cm³, a melt index ($I_2$), measured at 190° C. and 2.16 kg, of approximately 0.68 g/10 minutes, an melt flow ratio ($I_{10}/I_2$) of approximately 6.8. Additional properties of IPC-3 were measured, and are reported in Table 2.

IPC-3 was prepared via solution polymerization in a dual loop reactor system in the presence of a first catalyst system, as described below, in the first and a second catalyst system, as described below, in the second reactor.

The first catalyst system comprises bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula:

The polymerization conditions for IPC-3 are reported in Table 1. Referring to Table 1, MMAO is modified methyl aluminoxane; and RIBS-2 is bis(hydrogenated tallow alkyl) methyl, tetrakis(pentafluorophenyl)borate(1-)amine, used as cocatalysts.

Comparative Polyolefin Composition 1

Comparative polyolefin composition 1 (CPC-1) comprises an ethylene-octene interpolymer, having a density of approximately 0.917 g/cm³, a melt index ($I_2$), measured at 190° C. and 2.16 kg, of approximately 0.99 g/10 minutes, an melt flow ratio ($I_{10}/I_2$) of approximately 8.4. Additional properties of CPC-1 are reported in Table 2. CPC-1 was prepared via solution polymerization in a dual loop reactor system.

Comparative Polyolefin Composition 2

Comparative polyolefin composition 2 (CPC-2) comprises an ethylene-hexene interpolymer, having a density of approximately 0.919 g/cm³, a melt index ($I_2$), measured at 190° C. and 2.16 kg, of approximately 0.94 g/10 minutes, an melt flow ratio ($I_{10}/I_2$) of approximately 5.6. Additional properties of CPC-2 are reported in Table 2. CPC-2 was prepared via gas phase polymerization in a single fluidized bed reactor system.

TABLE 1

| Sample # | Units | IPC-1 | IPC-2 | IPC-3 |
|---|---|---|---|---|
| REACTOR FEEDS | | | | |
| Rx1 Total Solvent Flow | lb/hr | 999 | 1171 | 1057 |
| Rx1 Fresh Ethylene Flow | lb/hr | 181 | 213 | 183 |
| Rx1 Total Ethylene Flow | lb/hr | 189 | 222 | 191 |
| Rx1 Fresh Comonomer Flow | lb/hr | 33 | 29 | 35 |
| Rx1 Total Comonomer Flow | lb/hr | 75 | 67 | 77 |
| Rx1 Feed Solvent/Ethylene Ratio | Ratio | 5.51 | 5.49 | 5.78 |
| Rx1 Hydrogen Mole Percent | mol % | 1.01 | 1.00 | 0.78 |
| Rx2 Total Solvent Flow | lb/hr | 364 | 239 | 385 |
| Rx2 Fresh Ethylene Flow | lb/hr | 135 | 89 | 144 |
| Rx2 Total Ethylene Flow | lb/hr | 138 | 91 | 147 |
| Rx2 Fresh Comonomer Flow | lb/hr | 0 | 0 | 0 |
| Rx2 Total Comonomer Flow | lb/hr | 16 | 8 | 16 |
| Rx2 Feed Solvent/Ethylene Ratio | Ratio | 2.69 | 2.68 | 2.67 |
| Rx2 Hydrogen Mole Percent | mol % | 2.17 | 2.79 | 1.74 |
| REACTION | | | | |
| Rx1 Control Temperature | °C. | 130 | 140 | 130 |
| Rx1 Exit Comonomer Concentration | g/L | 23.2 | 16.9 | 23.1 |
| Rx1 Ethylene Conversion | % | 79.7 | 78.7 | 82.1 |
| Rx1 FTnIR Exit C2 Conc. (raw) | g/L | 19.7 | 20.1 | 17.2 |
| Rx1 FTnIR Exit C2 Conc. (cor.) | g/L | 19.7 | 20.1 | 17.2 |
| Rx1 FTnIR Correction Factor | g/L | 0.0 | 0.0 | 0.0 |
| Rx1 Log Viscosity | — | 3.30 | 3.16 | 3.46 |
| Rx1 Viscosity | cP | 1993 | 1450 | 2894 |
| Rx2 Control Temperature | °C. | 189 | 170 | 190 |
| Rx2 Exit Comonomer Concentration | g/L | 9.8 | 9.8 | 10.2 |
| Rx2 Ethylene Conversion | % | 72.2 | 67.0 | 71.7 |
| Rx2 FTnIR Exit C2 Conc (raw) | g/L | 20.8 | 17.0 | 19.5 |
| Rx2 FTnIR Exit C2 Conc (cor) | g/L | 17.1 | 16.2 | 17.0 |
| Rx2 FTnIR Correction Factor | g/L | -3.7 | -0.8 | -2.5 |
| Rx2 Log Viscosity | — | 2.72 | 2.90 | 2.80 |
| Rx2 Viscosity | cP | 530 | 790 | 627 |
| Rx1 Split | % | 60 | 70 | 60 |
| CATALYST | | | | |
| Rx1 Catalyst Efficiency | Lb Polymer/Lb catalyst metal | 23,070,000 | 16,735,402 | 10,899,536 |
| Rx1 RIBS-2 Molar Ratio | Ratio | 3.3 | 2.0 | 1.7 |
| Rx1 MMAO Molar Ratio | Ratio | 81 | >100 | 12 |
| Rx2 Catalyst Efficiency | Lb Polymer/Lb catalyst metal | 22,000,000 | 18,500,000 | 3,999,069 |
| Rx2 RIBS-2 Molar Ratio | Ratio | 3.7 | 4.2 | 1.9 |
| Rx2 MMAO Molar Ratio | Ratio | >100 | >100 | 10 |

TABLE 2

| Properties | Units | Method | IPC-1 | IPC-2 | IPC-3 | CPC-1 | CPC-2 |
|---|---|---|---|---|---|---|---|
| Density | g/cm$^3$ | ASTM D792 Method B | 0.919 | 0.918 | 0.918 | 0.917 | 0.919 |
| $I_2$ | g 10/min | ASTM D1238 | 0.96 | 0.74 | 0.68 | 0.99 | 0.94 |
| $I_{10}$ | g/10 min | ASTM D1238 | 6.01 | 4.45 | 4.59 | 8.32 | 5.32 |
| $I_{10}/I_2$ | Calculated | | 6.3 | 6.1 | 6.8 | 8.4 | 5.6 |
| Octene wt % | Wt. % | 13C NMR | 9.7 | 9 | Not determined | 10.8 | |
| Hexene wt % | Wt. % | 13C NMR | | | Not determined | | 6.2 |
| Heat of Crystallization | J/g | DSC | 145 | 140 | 139 | 139 | 142 |
| Heat of Fusion | J/g | DSC | 146 | 142 | 141 | 141 | 144 |
| Tc1 | °C. | DSC | 108.9 | 106.2 | 106.8 | 104.4 | 105.7 |
| Tm1 | °C. | DSC | 126.9 | 125.5 | 126.0 | 122.1 | 117.9 |
| Mn | g/mol | Conventional GPC | 53,874 | 57,071 | 47,428 | 30,566 | 48,268 |
| Mw | g/mol | Conventional GPC | 113,674 | 119,762 | 119,674 | 104,070 | 113,789 |
| Mz | g/mol | Conventional GPC | 208,923 | 217,243 | 233,940 | 245,313 | 202,071 |

TABLE 2-continued

| Properties | Units | Method | IPC-1 | IPC-2 | IPC-3 | CPC-1 | CPC-2 |
|---|---|---|---|---|---|---|---|
| Mw/Mn | | Calculated | 2.1 | 2.1 | 2.5 | 3.4 | 2.4 |
| $\eta^*$ @ 0.1 rad/s | Pa.s | DMS | 9,304 | 8,454 | 10,526 | 9,879 | 6,797 |
| $[\eta^*$ @ 0.1( rad/s)]/$[\eta^*$ @ 100 (rad/s)] | | DMS | 3.7 | 3.1 | 4.7 | 6.7 | 2.8 |
| Tan Delta @ 0.1 rad/s | | DMS | 18.0 | 29.0 | 14.3 | 4.8 | 44.5 |
| Eta 0 | Pa.s | Creep, zero shear viscosity | 7,918 | 10,571 | 11,954 | 13,149 | 7,421 |
| ZSVR | | Calculated | 1.22 | 1.34 | 1.52 | 2.79 | 1.14 |
| Comonomer Dist.Index | | CDC Method | 0.551 | 0.658 | 0.559 | 0.670 | 0.709 |
| Stdev | °C. | CDC Method | 25.4 | 12.8 | 25.1 | 14.2 | 7.8 |
| Half Width | °C. | CDC Method | 4.5 | 4.3 | 3.9 | 29.8 | 16.6 |
| Half Width Stdev | | CDC Method | 0.177 | 0.335 | 0.155 | 2.09 | 2.12 |
| CDC | | CDC Method | 312 | 196 | 360 | 32 | 33 |
| Vinyl/1000 C. | | 1H NMR | 0.02 | 0.02 | Not determined | 0.22 | 0.07 |
| Cis/trans Vinylene/1000 C. | | 1H NMR | 0.05 | 0.05 | Not determined | 0.1 | 0.08 |
| Trisubstituted/ 1000 C. | | 1H NMR | Not detected | Not detected | Not determined | 0.04 | 0.05 |
| Vinylidene/ 1000 C. | | 1H NMR | Not detected | Not detected | Not determined | 0.04 | 0.02 |
| Total Unsaturation/ 1000 C. | | 1H NMR | 0.07 | 0.07 | Not determined | 0.39 | 0.22 |
| Thickness Normalized Intrinsic Elmendorf Tear | g/mil | ASTM D1922 | 517 | 462 | 455 | 467 | 348 |

Note:
Among the un-saturation species values determined by 1H NMR, cells marked not detected denote that the unsaturation was not detected at a limit of detection 0.001/1000 carbons.

Monolayer Blown Films

Monolayer blown films were produced from the Inventive Polyolefin Compositions 1-3 and Comparative Polyolefin Compositions 1-2, into Inventive Monolayer Films 1-3 (IMF 1-3) and Comparative Monolayer Films 1-2 (CMF 1-2), respectively, via an Egan Davis Standard extruder, equipped with a semi grooved barrel of ID 3.5 inch; 30/1 L/D ratio; a barrier screw, and an Alpine air ring. The extrusion line has an 8 inch die with internal bubble cooling. The extrusion line also has a film thickness gauge scanner. The film fabrication conditions were: film thickness maintained at 1 mil (0.001 in or 0.0254 mm); blow up ratio (BUR) 2.5; die gap 90 mil; and frost line height (FLH) 30 inch. Additional film fabrication conditions are given in Table 3. Additional film properties are reported in Table 5.

low density polyethylene (LDPE) and Comparative Polyolefin Compositions 1-2, which are further blended with low density polyethylene (LDPE), into Inventive Monolayer Films 1a-3a (IMF 1a-3a) and Comparative Monolayer Films 1a-2a (CMF 1a-2a), respectively, via an Egan Davis Standard extruder, equipped with a semi grooved barrel of ID 3.5 inch; 30/1 L/D ratio; a barrier screw, and an Alpine air ring. The extrusion line has an 8 inch die with internal bubble cooling. The extrusion line also has a film thickness gauge scanner. The film fabrication conditions were: film thickness maintained at 1 mil (0.001 in or 0.0254 mm); blow up ratio (BUR) 2.5; die gap 90 mil; and frost line height (FLH) 30 inch. Additional film fabrication conditions are given in Table 4. The LDPE comprised 20 percent of the total composition.

TABLE 3

| Property | Units | IMF-1 | IMF-2 | IMF-2 | CMF-1 | CMF-2 |
|---|---|---|---|---|---|---|
| Actual Rate | lbs/hr | 263 | 261 | 264 | 261 | 258 |
| Actual Rate (per in. of Circumference of Die) | lbs/inch of die circ. | 10.44 | 10.37 | 10.50 | 10.38 | 10.27 |
| Melt Temperature | F. | 411.3 | 418.1 | 430.3 | 399.8 | 412.6 |
| Head Pressure | psi | 4260 | 4680 | 4180 | 4020 | 4720 |
| Air Ring Blower Speed | % | 54.9 | 57.7 | 52.9 | 56.0 | 57.9 |

Monolayer Blown Films

Monolayer blown films were produced from Inventive Polyolefin Compositions 1-3, which are further blended with The LDPE had melt index $I_2$ of 2 g/10 minutes, and density of 0.919 g/cm³. Additional film properties are reported in Table 6.

TABLE 4

| Property | Units | IMF-1a | IMF-2a | IMF-3a | CMF-1a | CMF-2a |
|---|---|---|---|---|---|---|
| Actual Rate | lbs/hr | 261.25 | 261.625 | 258.25 | 259.75 | 259 |
| Actual Rate (per in. of Circumference of Die) | lbs/inch of die circ. | 10.391 | 10.406 | 10.271 | 10.331 | 10.301 |
| Air Ring Blower Speed | % | 53.1 | 53.1 | 48.1 | 56.9 | 54.9 |
| Head Pressure | psi | 4140 | 4480 | 3870 | 3690 | 4430 |
| Melt Temp | ° F. | 406.75 | 405.5 | 422 | 396.125 | 408 |

TABLE 5

| Properties | Units | Method | IMF-1 | IMF-2 | IMF-3 | CMF-1 | CMF-2 |
|---|---|---|---|---|---|---|---|
| Dart Type | | ASTM D1709 | B | B | Between A & B | A | A |
| Dart Drop Impact | g | ASTM D1709 | 436 | 484 | Between Dart A & B | 697 | 934 |
| Puncture | ft * lbf/in^3 | Internal method | 330 | 456 | 365 | 287 | 351 |
| Thickness Normalized MD Elmendorf Tear | g/mil | ASTM D1922 | 373 | 306 | 285 | 272 | 282 |

MD = machine direction.

TABLE 6

| Property | Units | Method | IMF-1a | IMF-2a | IMF-3a | CMF-1a | CMF-2a |
|---|---|---|---|---|---|---|---|
| Dart Type | | ASTM D1709 | A | A | A | A | A |
| Dart Drop Impact | g | ASTM D1709 | 406 | 367 | 376 | 271 | 253 |
| Puncture | ft * lbf/in^3 | Internal method | 318 | 383 | 277 | 289 | 286 |
| Thickness Normalized MD Elmendorf Tear | g/mil | ASTM D1922 | 180 | 154 | 128 | 126 | 141 |

MD = machine direction.

Co-Extruded Multilayer Films

The co-extruded multilayer blown films were fabricated on a Hosokawa Alpine 7-layer blown film extrusion machine, based on the formulation components reported in Table 7. This extrusion machine consists of seven 50 mm, 30:1 L/D, grooved feed extruders utilizing barrier screws and a 7.87 inch co-ex die. The die is equipped with internal bubble cooling.

The film fabrication conditions were: film thickness maintained at 4.5 mil; blow up ratio (BUR) 1.71; die gap 78.7 mil; and frost line height (FLH) 35 inch. Additional film fabrication conditions are given in Table 8. The co-extruded multilayer film properties are reported in Tables 9. Properties of bags fabricated from the co-extruded multilayer films are reported in Table 10.

TABLE 7

| Layer Composition | Layer Thickness (mil) |
|---|---|
| 80% LLDPE + 20% by weight LDPE | 1.2 |
| 80% LLDPE + 20% by weight HDPE | 2.1 |
| 80% LLDPE + 20% by weight LDPE | 1.2 |

LLDPE=Linear low density polyethylene=Inventive or Comparative Resin

LDPE=Low density polyethylene having melt index $I_2$ of 0.25 g/10 minutes, and density of 0.920 g/cm³.

HDPE=High density polyethylene melt index $I_2$ of 0.8 g/10 minutes, and density of 0.961 g/cm³.

TABLE 8

| Properties | Units | Inventive 1 Co-Ex Film | Inventive 2 Co-Ex Film | Comparative 1 Co-Ex Film | Comparative 2 Co-Ex Film |
|---|---|---|---|---|---|
| Actual Rate | lbs/hr | 325 | 325 | 325 | 324 |
| Actual Rate (per in. of die circumference) | lbs/inch of die circum. | 13.13 | 13.15 | 13.13 | 13.11 |
| Air Ring Blower Speed | % | 40 | 40 | 39 | 40 |
| Melt temperature - Extruder 1 | F. | 470 | 472 | 464 | 467 |
| Melt temperature - Extruder 2 | F. | 468 | 468 | 465 | 467 |
| Melt temperature - Extruder 3 | F. | 478 | 487 | 464 | 473 |
| Melt temperature - Extruder 4 | F. | 472 | 478 | 456 | 463 |
| Melt temperature - Extruder 5 | F. | 462 | 470 | 448 | 456 |
| Melt temperature - Extruder 6 | F. | 469 | 469 | 468 | 467 |
| Melt temperature - Extruder 7 | F. | 456 | 460 | 449 | 454 |
| Melt pressure - Extruder 1 | psi | 4,338 | 5,071 | 3,817 | 4,487 |
| Melt pressure - Extruder 2 | psi | 4,923 | 5,673 | 4,134 | 5,216 |
| Melt pressure - Extruder 3 | psi | 5,239 | 5,928 | 4,500 | 5,505 |

TABLE 8-continued

| Properties | Units | Inventive 1 Co-Ex Film | Inventive 2 Co-Ex Film | Comparative 1 Co-Ex Film | Comparative 2 Co-Ex Film |
|---|---|---|---|---|---|
| Melt pressure - Extruder 4 | psi | 6,555 | 7,188 | 5,426 | 6,689 |
| Melt pressure - Extruder 5 | psi | 5,173 | 5,884 | 4,351 | 5,324 |
| Melt pressure - Extruder 6 | psi | 5,169 | 6,039 | 4,676 | 5,631 |
| Melt pressure - Extruder 7 | psi | 5,918 | 6,856 | 5,192 | 6,369 |

The physical properties of the co-extruded multilayer films fabricated from the comparative and inventive samples are reported in Table 9.

TABLE 9

| Property | Dart Drop Impact (Dart B) | Puncture | Normalized MD Elmendorf Tear | 2% MD Secant Modulus | Total Haze |
|---|---|---|---|---|---|
| Units | g | ft*lbf/in^3 | g/mil | psi | % |
| Method | ASTM D1709 | Internal | ASTM D1922 | ASTM D882 | ASTM D1003 |
| Inventive 1 | 808 | 111 | 298 | 42,096 | 20 |
| Inventive 2 | 892 | 133 | 291 | 41,478 | 16 |
| Comparative 1 | 576 | 117 | 277 | 35,080 | 19 |
| Comparative 2 | 632 | 130 | 220 | 39,388 | 14 |

MD = machine direction.

Bags with fifty pound holding capacity were fabricated from the co-extruded multilayer inventive and comparative resin films. The bags were filled, sealed and subjected to the bag drop test. The results of the drop test are reported in Table 10.

TABLE 10

| Sample | Number of Passed Bags | Number of Failed Bags |
|---|---|---|
| Inventive 1 Co-ex film bags | 5 | 0 |
| Inventive 2 Co-ex film bags | 5 | 0 |
| Comparative 1 Co-ex film bags | 4 | 1 |
| Comparative 2 Co-ex film bags | 3 | 2 |

Test Methods

Test methods include the following:
Density

Samples that are measured for density are prepared according to ASTM D4703. Measurements are made within one hour of sample pressing using ASTM D792, Method B.
Melt Index Melt index ($I_2$) is measured in accordance with ASTM D1238, Condition 190° C./2.16 kg, and is reported in grams eluted per 10 minutes. Melt flow rate ($I_{10}$) is measured in accordance with ASTM D1238, Condition 190° C./10 kg, and is reported in grams eluted per 10 minutes.
Differential Scanning Calorimetry (DSC)

DSC can be used to measure the melting and crystallization behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (~25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 150° C. (this is the "second heat" ramp) at a 10° C./minute heating rate.

The cooling and second heating curves are recorded. The cool curve is analyzed by setting baseline endpoints from the beginning of crystallization to −20° C. The heat curve is analyzed by setting baseline endpoints from −20° C. to the end of melt. The values determined are peak melting temperature ($T_m$), peak crystallization temperature ($T_c$), heat of fusion ($H_f$) (inJ/g), and heat of crystallization (J/g)

The heat of fusion ($H_f$) and the peak melting temperature are reported from the second heat curve. Peak crystallization temperature and heat of crystallization is determined from the cooling curve.
Dynamic Mechanical Spectroscopy (DMS) Frequency Sweep Samples were compression-molded into 3 mm thick×25 mm diameter circular plaques at 177° C. for 5 minutes under 10 MPa pressure in air. The sample was then taken out of the press and placed on the counter to cool.

Constant temperature frequency sweep measurements were performed on an ARES strain controlled rheometer (TA Instruments) equipped with 25 mm parallel plates, under a nitrogen purge. For each measurement, the rheometer was thermally equilibrated for at least 30 minutes prior to zeroing the gap. The sample was placed on the plate and allowed to melt for five minutes at 190° C. The plates were then closed to 2 mm, the sample trimmed, and then the test was started. The method has an additional five minute delay built in, to allow for temperature equilibrium. The experiments were performed at 190° C. over a frequency range of 0.1-100 rad/s at five points per decade interval. The strain amplitude was constant at 10%. The stress response was analyzed in terms of amplitude and phase, from which the storage modulus (G'), loss modulus (G"), complex modulus (G*), dynamic complex viscosity (η*), and tan (δ) or tan delta were calculated.
Conventional Gel Permeation Chromatography (GPC)

The GPC system consists of either a Polymer Laboratories Model PL-210 or a Polymer Laboratories Model PL-220 instrument equipped with a refractive index (RI) concentration detector. The column and carousel compartments are operated at 140° C. Three Polymer Laboratories 10-μm Mixed-B columns are used with the solvent 1,2,4-trichlorobenzene. The samples are prepared at a concentration of 0.1 g of polymer in 50 milliliters of solvent. The solvent used to prepare the samples contains 200 ppm of the antioxidant butylated hydroxytoluene (BHT). Samples are prepared by agitating lightly for four hours at 160° C. The injection volume used is 200 microliters and the flow rate is 1.0 ml/min. Calibration of the GPC column set is performed with twenty one narrow molecular weight distribution polystyrene standards purchased from Polymer Laboratories.

The polystyrene standard peak molecular weights ($M_{PS}$) are converted to polyethylene molecular weight ($M_{PE}$) using Equation 1. The equation is described in Williams and Ward, J. Polym. Sci., Polym. Letters, 6, 621 (1968)):

$$M_{PE} = A \times (M_{PS})^B \quad \text{Equation 1}$$

Where A has a value of 0.4316 and B is equal to 1.0.

A third order polynomial is determined to build the logarithmic molecular weight calibration as a function of elution volume.

Polyethylene equivalent molecular weight calculations were performed using PolymerChar "GPC One" software. The number average molecular weight (Mn), weight average molecular weight (Mw), and z-average molecular weight (Mz) was calculated by inputting the GPC results in equations 2 to 4:

$$\overline{Mn} = \frac{\sum\limits_i^i RI_i}{\sum\limits_i \left(\frac{RI_i}{M_{PE,i}}\right)} \quad \text{Equation 2}$$

$$\overline{Mw} = \frac{\sum\limits_i^i (RI_i * M_{PE,i})}{\sum\limits_i RI_i} \quad \text{Equation 3}$$

$$\overline{Mz} = \frac{\sum\limits_i^i (RI_i * M_{PE,i}^2)}{\sum (RI_i * M_{PE,i})} \quad \text{Equation 4}$$

Where $RI_i$ and $M_{PE,i}$ are the concentration detector baseline corrected response and conventional calibrated polyethylene molecular weight for the $i^{th}$ slice of the concentration response, elution volume paired data set. The precision of the weight-average molecular weight $\Delta Mw$ is <2.6%.

The MWD is expressed as the ratio of the weight average molecular weight (Mw) to the number average molecular weight (Mn).

The GPC column set is calibrated by running 21 narrow molecular weight distribution polystyrene standards. The molecular weight (MW) of the standards ranges from 580 to 8,400,000, and the standards are contained in 6 "cocktail" mixtures. Each standard mixture has at least a decade of separation between individual molecular weights. The standard mixtures are purchased from Polymer Laboratories. The polystyrene standards are prepared at 0.025 g in 50 mL of solvent for molecular weights equal to or greater than 1,000,000 and 0.05 g in 50 mL of solvent for molecular weights less than 1,000,000. The polystyrene standards were dissolved at 80° C. with gentle agitation for 30 minutes. The narrow standards mixtures are run first and in order of decreasing highest molecular weight component to minimize degradation.

CEF Method

Comonomer distribution analysis is performed with Crystallization Elution Fractionation (CEF) (PolymerChar in Spain, (B Monrabal et al, Macromol. Symp., 257, 71-79, 2007). Ortho-dichlorobenzene (ODCB) with 600 ppm antioxidant butylated hydroxytoluene (BHT) is used as solvent. Sample preparation is done with auto sampler at 160° C. for 2 hours under shaking at 4 mg/ml (unless otherwise specified). The injection volume is 300 µl. The temperature profile of CEF is: crystallization at 3° C./min from 110° C. to 30° C., the thermal equilibrium at 30° C. for 5 minutes, elution at 3° C./min from 30° C. to 140° C. The flow rate during crystallization is at 0.052 ml/min. The flow rate during elution is at 0.50 ml/min. The data is collected at one data point/second.

CEF column is packed by the Dow Chemical Company with glass beads at 125 µm±6% (MO-SCI Specialty Products) with ⅛ inch stainless tubing. Glass beads are acid washed by MO-SCI Specialty with the request from the Dow Chemical Company. Column volume is 2.06 ml. Column temperature calibration is performed by using a mixture of NIST Standard Reference Material Linear polyethylene 1475a (1.0 mg/ml), and Eicosane (2 mg/ml) in ODCB. Temperature is calibrated by adjusting elution heating rate so that NIST linear polyethylene 1475a has a peak temperature at 101.0° C., and Eicosane has a peak temperature of 30.0° C. The CEF column resolution is calculated with a mixture of NIST linear polyethylene 1475a (1.0 mg/ml) and hexacontane (Fluka, purum, ≥97.0%, 1 mg/ml). A baseline separation of hexacontane and NIST polyethylene 1475a is achieved. The area of hexacontane (from 35.0 to 67.0° C.) to the area of NIST 1475a from 67.0 to 110.0° C. is 50 to 50, the amount of soluble fraction below 35.0° C. is <1.8 wt %. The CEF column resolution is defined in equation 1, where the column resolution is 6.0.

$$\text{Resolution} = \frac{\text{Peak temperature of } NIST\ 1475a - \text{Peak Temperature of Hexacontane}}{\text{Half-height Width of } NIST\ 1475a + \text{Half-height Width of Hexacontane}} \quad \text{Equation 1}$$

Determination of Half Height and One Tenth Height of the CEF Elution Profile

The CEF instrument is calibrated according to the CEF Method described herein, and a plot of the relative IR detector signal is made as a function of temperature. A single baseline is subtracted from the IR measurement signal in order create a relative mass-elution profile plot starting and ending at zero relative mass at its lowest and highest elution temperatures (typically between 25° C. and 110° C.). For convenience, this plot (FIG. 1) plotted as a normalized quantity with an area equivalent to 100. In the relative mass-elution profile plot, peaks that represent an area of at least 25% of the total integrated signal between 35° C. and 110° C. degrees are assigned. Any peaks that do not return to the baseline by at least 10% of the relative mass-elution height (connected by more than 10% height at their lowest point), are defined as a single peak (no deconvolution or similar numerical methods are used to mathematically separate convoluted peaks). Each separate peak is then measured for width in ° C. at 50% of the maximum height of the peak in the mass-elution profile plot. Each separate peak is then measured for width ° C. at 10% of the maximum height in the mass-elution profile plot.

CDC Method

Comonomer distribution constant (CDC) is calculated from comonomer distribution profile by CEF. CDC is defined as Comonomer Distribution Index divided by Comonomer Distribution Shape Factor multiplying by 100 as shown in Equation 1.

$$CDC = \frac{\text{Comonomer Distribution Index}}{\text{Comonomer Distribution Shape Factor}} = \qquad \text{Equation 1}$$

$$\frac{\text{Comonomer Distribution Index}}{\text{Half Width/Stdev}} * 100$$

Comonomer distribution index stands for the total weight fraction of polymer chains with the comonomer content ranging from 0.5 of median comonomer content ($C_{median}$) and 1.5 of $C_{median}$ from 35.0 to 119.0° C. Comonomer Distribution Shape Factor is defined as a ratio of the half width of comonomer distribution profile divided by the standard deviation of comonomer distribution profile from the peak temperature ($T_p$).

CDC is calculated from comonomer distribution profile by CEF, and CDC is defined as Comonomer Distribution Index divided by Comonomer Distribution Shape Factor multiplying by 100 as shown in Equation 1, and wherein Comonomer distribution index stands for the total weight fraction of polymer chains with the comonomer content ranging from 0.5 of median comonomer content ($C_{median}$) and 1.5 of $C_{median}$ from 35.0 to 119.0° C., and wherein Comonomer Distribution Shape Factor is defined as a ratio of the half width of comonomer distribution profile divided by the standard deviation of comonomer distribution profile from the peak temperature (Tp).

CDC is calculated according to the following steps:

(A) Obtain a weight fraction at each temperature (7) ($w_T$(T)) from 35.0° C. to 119.0° C. with a temperature step increase of 0.2° C. from CEF according to Equation 2.

$$\int_{35}^{119.0} w_T(T)dT = 1 \qquad \text{Equation 2}$$

(B) Calculate the median temperature ($T_{median}$) at cumulative weight fraction of 0.500, according to Equation 3.

$$\int_{35}^{T_{median}} w_T(T)dT = 0.5 \qquad \text{Equation 3}$$

(C) Calculate the corresponding median comonomer content in mole % ($C_{median}$) at the median temperature ($T_{median}$) by using comonomer content calibration curve according to Equation 4.

$$\ln(1 - \text{comonomercontent}) = -\frac{207.26}{273.12 + T} + 0.5533 \qquad \text{Equation 4}$$

$$R^2 = 0.997$$

(D) Construct a comonomer content calibration curve by using a series of reference materials with known amount of comonomer content, i.e., eleven reference materials with narrow comonomer distribution (mono-modal comonomer distribution in CEF from 35.0 to 119.0° C.) with weight average Mw of 35,000 to 115,000 (measured via conventional GPC) at a comonomer content ranging from 0.0 mole % to 7.0 mole % are analyzed with CEF at the same experimental conditions specified in CEF experimental sections;

(E) Calculate comonomer content calibration by using the peak temperature ($T_p$) of each reference material and its comonomer content. The calibration is calculated from each reference material as shown in Equation 4 wherein: $R^2$ is the correlation constant.

(F) Calculate Comonomer Distribution Index from the total weight fraction with a comonomer content ranging from 0.5*$C_{median}$ to 1.5*$C_{median}$, and if $T_{median}$ is higher than 98.0° C., Comonomer Distribution Index is defined as 0.95.

(G) Obtain Maximum peak height from CEF comonomer distribution profile by searching each data point for the highest peak from 35.0° C. to 119.0° C. (if the two peaks are identical, then the lower temperature peak is selected); half width is defined as the temperature difference between the front temperature and the rear temperature at the half of the maximum peak height, the front temperature at the half of the maximum peak is searched forward from 35.0° C., while the rear temperature at the half of the maximum peak is searched backward from 119.0° C., in the case of a well defined bimodal distribution where the difference in the peak temperatures is equal to or greater than the 1.1 times of the sum of half width of each peak, the half width of the inventive ethylene-based polymer composition is calculated as the arithmetic average of the half width of each peak; and (H) Calculate the standard deviation of temperature (Stdev) according Equation 5

$$\text{Stdev} = \sqrt{\sum_{35.0}^{119.0} (T - T_p)^2 * w_T(T)} \qquad \text{Equation 5}$$

Creep Zero Shear Viscosity Measurement Method

Zero-shear viscosities are obtained via creep tests that were conducted on an AR-G2 stress controlled rheometer (TA Instruments; New Castle, Del.) using 25-mm-diameter parallel plates at 190° C. The rheometer oven is set to test temperature for at least 30 minutes prior to zeroing fixtures. At the testing temperature a compression molded sample disk is inserted between the plates and allowed to come to equilibrium for 5 minutes. The upper plate is then lowered down to 50 μm above the desired testing gap (1.5 mm) Any superfluous material is trimmed off and the upper plate is lowered to the desired gap. Measurements are done under nitrogen purging at a flow rate of 5 L/min Default creep time is set for 2 hours.

A constant low shear stress of 20 Pa is applied for all of the samples to ensure that the steady state shear rate is low enough to be in the Newtonian region. The resulting steady state shear rates are in the range of $10^{-3}$ to $10^{-4}$ $s^{-1}$ for the samples in this study. Steady state is determined by taking a linear regression for all the data in the last 10% time window of the plot of log (J(t)) vs. log(t), where J(t) is creep compliance and t is creep time. If the slope of the linear regression is greater than 0.97, steady state is considered to be reached, then the creep test is stopped. In all cases in this study the slope meets the criterion within 2 hours. The steady state shear rate is determined from the slope of the linear regression of all of the data points in the last 10% time window of the plot of ε vs. t, where ε is strain. The zero-shear viscosity is determined from the ratio of the applied stress to the steady state shear rate.

In order to determine if the sample is degraded during the creep test, a small amplitude oscillatory shear test is conducted before and after the creep test on the same specimen from 0.1 to 100 rad/s. The complex viscosity values of the two tests are compared. If the difference of the viscosity values at 0.1 rad/s is greater than 5%, the sample is considered to have degraded during the creep test, and the result is discarded.

Zero-Shear Viscosity Ratio (ZSVR) is defined as the ratio of the zero-shear viscosity (ZSV) of the branched polyethylene material to the ZSV of the linear polyethylene material at the equivalent weight average molecular weight (Mw-gpc) according to the following Equations 1 and 2:

$$ZSVR = \frac{\eta_{0B}}{\eta_{0L}} \qquad \text{Equation 1}$$

$$\eta_{0L} = 2.29 \times 10^{-15} M_{w\text{-}gpc}^{3.65} \qquad \text{Equation 2}$$

The ZSV value is obtained from creep test at 190° C. via the method described above. The Mw-gpc value is determined by the conventional GPC method (Equation 3 in the Conventional GPC method description). The correlation between ZSV of linear polyethylene and its Mw-gpc was established based on a series of linear polyethylene reference materials. A description for the ZSV-Mw relationship can be found in the ANTEC proceeding: Karjala, Teresa P., Sammler, Robert L., Mangnus, Marc A., Hazlitt, Lonnie G., Johnson, Mark S., Hagen, Charles M. Jr., Huang, Joe W. L., Reichek, Kenneth N., "Detection of low levels of long-chain branching in polyolefins", Annual Technical Conference—Society of Plastics Engineers (2008), 66th 887-891.

$^1$H NMR Method 3.26 g of stock solution is added to 0.133 g of polyolefin sample in 10 mm NMR tube. The stock solution is a mixture of tetrachloroethane-d$_2$ (TCE) and perchloroethylene (50:50, w: w) with 0.001M Cr$^{3+}$. The solution in the tube is purged with N$_2$ for 5 minutes to reduce the amount of oxygen. The capped sample tube is left at room temperature overnight to swell the polymer sample. The sample is dissolved at 110° C. with shaking. The samples are free of the additives that may contribute to unsaturation, e.g. slip agents such as erucamide.

The $^1$H NMR are run with a 10 mm cryoprobe at 120° C. on Bruker AVANCE 400 MHz spectrometer.

Two experiments are run to get the unsaturation: the control and the double presaturation experiments.

For the control experiment, the data is processed with exponential window function with LB=1 Hz, baseline was corrected from 7 to −2 ppm. The signal from residual $^1$H of TCE is set to 100, the integral $I_{total}$ from −0.5 to 3 ppm is used as the signal from whole polymer in the control experiment. The number of CH$_2$ group, NCH$_2$, in the polymer is calculated as following:

$$NCH_2 = I_{total}/2 \qquad \text{Equation 1}$$

For the double presaturation experiment, the data is processed with exponential window function with LB=1 Hz, baseline was corrected from 6.6 to 4.5 ppm. The signal from residual $_1$H of TCE is set to 100, the corresponding integrals for unsaturations ($I_{vinylene}$, $I_{trisubstituted}$, $I_{vinyl}$ and $I_{vinylidene}$) were integrated based on the region shown in FIG. 6. The number of unsaturation unit for vinylene, trisubstituted, vinyl and vinylidene are calculated:

$$N_{vinylene} = I_{vinylene}/2 \qquad \text{Equation 2}$$

$$N_{trisubstituted} = I_{trisubstitute} \qquad \text{Equation 3}$$

$$N_{vinyl} = I_{vinyl}/2 \qquad \text{Equation 4}$$

$$N_{vinylidene} = I_{vinylidene}/2 \qquad \text{Equation 5}$$

The unsaturation unit/1,000 carbons are calculated as following:

$$N_{vinylene}/1,000C = (N_{vinylene}/NCH_2)*1,000 \qquad \text{Equation 6}$$

$$N_{trisubstituted}/1,000C = (N_{trisubstituted}/NCH_2)*1,000 \qquad \text{Equation 7}$$

$$N_{vinyl}/1,000C = (N_{vinyl}/NCH_2)*1,000 \qquad \text{Equation 8}$$

$$N_{vinylidene}/1,000C = (N_{vinylidene}/NCH_2)*1,000 \qquad \text{Equation 9}$$

The chemical shift reference is set at 6.0 ppm for the $^1$H signal from residual proton from TCT-d2. The control is run with ZG pulse, TD 32768, NS 4, DS 12, SWH 10,000 Hz, AQ 1.64 s, D1 14s. The double presaturation experiment is run with a modified pulse sequence, O1P 1.354 ppm, O2P 0.960 ppm, PL9 57db, PL21 70 db, TD 32768, NS 200, DS 4, SWH 10,000 Hz, AQ 1.64s, D1 1 s, D13 13s. The modified pulse sequences for unsaturation with Bruker AVANCE 400 MHz spectrometer are shown in FIG. 7.

$^{13}$C NMR Method

The samples were prepared by adding approximately 2.74 g of of tetrachloroethane-d$_2$ containing 0.025 M Cr (AcAc)$_3$ to 0.2 g sample in a Norell 1001-7 10 mm NMR tube. Oxygen was removed by manually purging tubes with nitrogen using a Pasteur pipette for 1 minute. The samples were dissolved and homogenized by heating the tube and its contents to ~150° C. using a heating block with minimal use of heat gun. Each sample was visually inspected to ensure homogeneity. Samples were thoroughly mixed immediately prior to analysis, and were not allowed to cool before insertion into the heated NMR probe. This is necessary to ensure the sample is homogeneous and representative of the whole. The data were collected using a Bruker 400 MHz spectrometer equipped with a Bruker cryoprobe. The data were acquired using 160 scans, a 6 sec pulse repetition delay with a sample temperature of 120° C. All measurements were made on non-spinning samples in locked mode. Samples were allowed to thermally equilibrate for 7 minutes prior to data acquisition. The $^{13}$C NMR chemical shifts were internally referenced to the EEE triad at 30 ppm.

Melt Strength Measurement

The melt strength was measured at 190° C. on the Rheotens Model 71.97 Melt Strength Tester. The melt was produced by a Goettfert Rheotester 2000 capillary rheometer with a flat, 30/2 die, at a shear rate of 38.2 s$^{-1}$. The barrel of the rheometer (diameter: 12 mm) was filed in less than one minute. A delay of 10 minutes was allowed for proper melting. The take-up speed of the Rheotens wheels was varied, with a constant acceleration of 2.4 mm/sec$^2$. The tension in the drawn strand was monitored with time, until the strand broke. The steady-state force and the velocity at break were reported.

Intrinsic Elmendorf Tear

The Elmendorf Tear test determines the average force to propagate tearing through a specified length of plastic film or non rigid sheeting after the tear has been started, using an Elmendorf-type tearing tester.

The sample intrinsic tear is measured per ASTM D1922 on compression molded plaques. The plaques are molded per ASTM D4703 Procedure C Annex 1 (controlled cooling at 15° C./min) Final thickness of the intrinsic tear samples is targeted to be in the range from 10 to 12 mil. Details of the ASTM D1922 are given in the following section. Prior to testing, the specimen thickness is measured at the plaque center. A total of 15 specimens per resin sample are tested and the average tear strength and average thickness reported. The average tear strength is normalized to the average thickness.

Monolayer and Co-Extruded Multilayer Blown Film Tests

The following monolayer and multilayer blown film properties were measured

ASTM D1003 Total Haze

Samples measured for internal haze and overall (total) haze are sampled and prepared according to ASTM D1003. Internal haze was obtained via refractive index matching using mineral oil on both sides of the films. A Hazeguard Plus (BYK-Gardner USA; Columbia, Md.) is used for testing. Surface haze is determined as the difference between total haze and internal haze. The total haze is reported as the average of five measurements.

ASTM D1922 MD (Machine Direction) and CD (Cross Direction) Elmendorf Tear Type B The Elmendorf Tear test determines of the average force to propagate tearing through a specified length of plastic film or non rigid sheeting after the tear has been started, using an Elmendorf-type tearing tester.

After film production from the sample to be tested, the film is conditioned for at least 40 hours at 23° C. (+/−2° C.) and 50% R.H (+/−5) as per ASTM standards. Standard testing conditions are 23° C. (+/−2° C.) and 50% R.H (+/−5) as per ASTM standards.

The force in grams required to propagate tearing across a film or sheeting specimen is measured using a precisely calibrated pendulum device. In the test, acting by gravity, the pendulum swings through an arc, tearing the specimen from a precut slit. The specimen is held on one side by the pendulum and on the other side by a stationary member. The loss in energy by the pendulum is indicated by a pointer or by an electronic scale. The scale indication is a function of the force required to tear the specimen.

The sample specimen geometry used in the Elmendorf tear test is the 'constant radius geometry' as specified in ASTM D1922. Testing is typically carried out on specimens that have been cut from both the film MD and CD directions. Prior to testing, the film specimen thickness is measured at the sample center. A total of 15 specimens per film direction are tested and the average tear strength and average thickness reported. The average tear strength is normalized to the average thickness.

ASTM D882 MD and CD 2% Secant Modulus

The film MD (Machine Direction) and CD (Cross Direction) secant modulus was determined per ASTM D882. The reported secant modulus value is the average of five measurements.

Puncture Internal Method

The Puncture test determines the resistance of a film to the penetration of a probe at a standard low rate, a single test velocity.

The internal puncture test method is based on ASTM D5748.

After film production, it is conditioned for at least 40 hours at 23° C. (+/−2° C.) and 50% R.H (+/−5) as per ASTM standards. Standard testing conditions are 23° C. (+/−2° C.) and 50% R.H (+/−5) as per ASTM standards.

Puncture is measured on a tensile testing machine. Square specimens are cut from a sheet to a size of 6 inches by 6 inches. The specimen is clamped in a 4 inch diameter circular specimen holder and a puncture probe is pushed into the centre of the clamped film at a cross head speed of 10 inches/minute.

The internal test method follows ASTM D5748 with one modification. It deviates from the ASTM D5748 method in that the probe used is a 0.5 inch diameter polished steel ball on a 0.25 inch support rod (rather than the 0.75 inch diameter, pear shaped probe specified in D5748).

There is a 7.7 inch maximum travel length to prevent damage to the test fixture. There is no gauge length; prior to testing, the probe is as close as possible to but not touching the specimen.

A single thickness measurement is made in the centre of the specimen. For each specimen, the maximum force, force at break, penetration distance and energy to break is determined. A total of five specimens are tested to determine an average puncture value. The puncture probe is cleaned using a "Kim-wipe" after each specimen.

ASTM D1709 Dart Drop

The film Dart Drop test determines the energy that causes plastic film to fail under specified conditions of impact by a free falling dart. The test result is the energy, expressed in terms of the weight of the missile falling from a specified height, which would result in failure of 50% of the specimens tested.

After the film is produce, it is conditioned for at least 40 hours at 23° C. (+/−2° C.) and 50% R.H (+/−5) as per ASTM standards. Standard testing conditions are 23° C. (+/−2° C.) and 50% R.H (+/−5) as per ASTM standards.

The test result is reported as either by Method A, which uses a 1.5" diameter dart head and 26" drop height, or by Method B, which uses a 2" diameter dart head and 60" drop height. The sample thickness is measured at the sample center and the sample then clamped by an annular specimen holder with an inside diameter of 5 inches. The dart is loaded above the center of the sample and released by either a pneumatic or electromagnetic mechanism.

Testing is carried out according to the 'staircase' method. If the sample fails, a new sample is tested with the weight of the dart reduced by a known and fixed amount. If the sample does not fail, a new sample is tested with the weight of the dart increased by a known amount. After 20 specimens have been tested the number of failures is determined. If this number is 10 then the test is complete. If the number is less than 10 then the testing continues until 10 failures have been recorded. If the number is greater than 10, testing is continued until the total of non-failures is 10. The Dart drop strength is determined from these data as per ASTM D1709 and expressed in grams as either the dart drop impact of Type A or Type B. In some cases, the sample dart drop impact strength may lie between A and B. In these cases it is not possible to obtain a quantitative dart value.

Bag Drop Test

Five, filled 50 lb bags, made from the 4.5 mil thick co-extruded film, are dropped from a height of 8 feet (2.4 meters). The bags are dropped three times each using the following protocol.
1) Drop on the bag side
2) Drop on the bag bottom
3) Drop on the bag face After each drop, the bags are inspected for any sign of failure. The test results are reported as 1) the total number of bags which passed, and 2) the total number of bags which failed the drop test.

We claim:

1. A polyolefin composition suitable for packaging applications comprising:

an ethylene/α-olefin interpolymer composition comprising (a) from 50 to 75 percent by weight of a first ethylene/α-olefin copolymer fraction having a density in the range of 0.894 to 0.908 g/cm$^3$, a melt index ($I_2$) in the range of from 0.2 to 1 g/10 minutes, and (b) from 25 to 50 percent by weight of a second ethylene/α-olefin copolymer fraction, wherein said ethylene/α-olefin interpolymer composition has a density in the range of 0.910 to 0.924 g/cm$^3$, a melt index ($I_2$) in the range of from 0.5 to 2 g/10 minutes, a zero shear viscosity ratio (ZSVR) in the range of from 1.15 to 2.5, a molecular weight distribution, expressed as the ratio of the weight average molecular weight to number average molecular weight ($M_w/M_n$) in the range of from 2.0 to 4.0, and tan delta at 0.1 radian/second and 190° C. in the range of from 6 to 43, wherein said ethylene/α-olefin interpolymer composition has at least 2 peaks on elution profile via crystallization elution fractionation (CEF) procedure, wherein each peak comprises at least 25 weight percent of the total area of the elution profile, wherein the separation of the 2 peak positions are in the range of from 20 to 40° C., wherein a higher elution temperature peak is at an elution temperature greater than 90° C., and wherein a lower elution temperature peak is at an elution temperature in the range of from 50 to 80° C., and wherein the width of the higher elution temperature peak at 50 percent peak height is less than 4° C., and wherein the width of the higher elution temperature peak at 10 percent peak height is less than 9° C., and wherein the width of the lower elution temperature peak at 50 percent peak height is less than 8° C., and wherein the width of the lower elution temperature peak at 10 percent peak height is less than 25° C.

2. The polyolefin composition of claim 1, wherein said ethylene/α-olefin interpolymer composition is characterized by one or more of the following:
   a. has a vinyl unsaturation of less than 0.1 vinyls per one thousand carbon atoms present in the backbone of the ethylene/α-olefin interpolymer composition; and/or
   b. has a tan delta at 0.1 radian/second, determined at 190° C., in the range of from 6 to 43; and/or
   c. has a comonomer distribution constant in the range of from 50 to 500.

3. The polyolefin composition of claim 1 further comprising one or more ethylene polymers, or one or more propylene based polymers, or combinations thereof.

4. A film comprising the polyolefin composition of claim 1.

5. A sheet comprising the polyolefin composition of claim 1.

6. The polyolefin composition of claim 1, wherein said polyolefin composition is characterized by at least two of the following:
   a. having a Dart impact A of at least 1000 g, measured according to ASTM D1709, when said polyolefin composition is formed into a monolayer blown film having a thickness of 1 mil;
   b. having a Dart impact B of at least 400 g, measured according to ASTM D1709, when said polyolefin composition is formed into a monolayer blown film having a thickness of 1 mil; and/or
   c. having a normalized machine direction Elmendorf tear of at least 250 g/mil, measured according to ASTM D1922, when said polyolefin composition is formed into a monolayer blown film having a thickness of 1 mil.

7. The polyolefin composition of claim 6, wherein said polyolefin composition further comprises 5 to 20 percent by weight of low density polyethylene (LDPE), and wherein the Dart Impact A is greater than 275 g measured according to ASTM D1709, when said polyolefin composition is formed into a monolayer blown film having a thickness of 1 mil.

8. A packaging device comprising the film of claim 4.

9. The polyolefin composition of claim 6, wherein said polyolefin composition further comprises 5 to 20 percent by weight of low density polyethylene (LDPE), and wherein the Dart Impact A is greater than 300 g measured according to ASTM D1709, when said polyolefin composition is formed into a monolayer blown film having a thickness of 1 mil.

10. A packaging device comprising the sheet of claim 5.

* * * * *